United States Patent
Keeney et al.

(10) Patent No.: US 8,834,365 B2
(45) Date of Patent: Sep. 16, 2014

(54) SKIN COLOR AND CAPACITIVE SENSOR SYSTEMS

(75) Inventors: Scott Keeney, Vancouver, WA (US); Zhe Huang, Fremont, CA (US)

(73) Assignee: nLIGHT Photonics Corporation, Vancouver, WA (US)

( * ) Notice: Subject to any disclaimer, the term of this patent is extended or adjusted under 35 U.S.C. 154(b) by 564 days.

(21) Appl. No.: 12/977,381

(22) Filed: Dec. 23, 2010

(65) Prior Publication Data
US 2012/0165682 A1    Jun. 28, 2012

(51) Int. Cl.
*A61B 5/00*   (2006.01)
*G01N 21/25*   (2006.01)
*A61B 18/20*   (2006.01)
*A61B 17/00*   (2006.01)
*A61B 18/00*   (2006.01)

(52) U.S. Cl.
CPC ............ *A61B 18/203* (2013.01); *G01N 21/251* (2013.01); *A61B 2017/00057* (2013.01); *A61B 2018/00476* (2013.01); *A61B 2018/00875* (2013.01); *A61B 2018/00029* (2013.01); *A61B 2018/00017* (2013.01); *A61B 5/441* (2013.01); *A61B 5/0059* (2013.01)
USPC ............................... 600/306; 600/476; 606/9

(58) Field of Classification Search
USPC ...................... 600/306, 476; 606/9
See application file for complete search history.

(56) References Cited

U.S. PATENT DOCUMENTS

| | | | |
|---|---|---|---|
| 5,595,568 A | 1/1997 | Anderson | |
| 5,735,844 A | 4/1998 | Anderson | |
| 7,118,563 B2 | 10/2006 | Weckwerth | |
| 7,413,567 B2 | 8/2008 | Weckwerth | |
| 7,452,356 B2 | 11/2008 | Grove | |
| 2007/0100401 A1 | 5/2007 | Lin | |
| 2009/0270848 A1* | 10/2009 | Weckwerth et al. | 606/9 |
| 2012/0041282 A1* | 2/2012 | Nichol et al. | 600/306 |

* cited by examiner

*Primary Examiner* — Charles A Marmor, II
*Assistant Examiner* — Etsub Berhanu
(74) *Attorney, Agent, or Firm* — Ethan A. McGrath

(57) ABSTRACT

A hair removal device utilizes a system for sensing the presence and color of skin. The system includes a skin color sensor assembly and a capacitive sensor assembly disposed in a housing. The skin color sensor assembly includes a light pipe communicating with a color sensor aperture of the housing and having one or more notches defining receiving and emitting light propagation regions, a color sensor and one or more light emitting diodes, and a holder having at least one standoff mated to the notches thereby directing light emitted by the light emitting diodes through the light pipe for reflection of an external surface and receipt by the sensor for detection of surface color. The capacitive sensor assembly includes a plurality of copper elements in proximity to a device aperture and contacting an interior surface of the housing and for detection of an object in contact with the copper elements.

11 Claims, 5 Drawing Sheets

SKIN COLOR AND CAPACITIVE SENSOR SYSTEMS

CROSS REFERENCE TO RELATED APPLICATION

Reference is hereby made to the following co-pending U.S. application dealing with related subject matter and assigned to the assignee of the present invention: "Single-Emitter Diode Based Light Homogenizing Apparatus And A Hair Removal Device Employing The Same," U.S. Ser. No. 12/976,466, filed Dec. 22, 2010.

BACKGROUND OF THE INVENTION

1. Field of the Invention

Generally, the field of the present invention relates to sensor systems. Specifically, the present invention relates to skin color and capacitive sensor systems for devices including hand-held consumer devices and assemblies thereof.

2. Background Art

Several devices and methods are presently used for the removal of hair on a person's body including applying hot wax to a target area and quickly removing the wax after the wax has cooled, shaving the target area with a razor, applying chemical depilatories to a target area, and applying laser radiation to a targeted area. There are significant advantages to the laser methods over the others with respect to the length of time it takes hair to grow back, ease of the process, etc. However, available laser hair removal devices tend to be far too bulky, unwieldy, and expensive for easy in-home use.

Many laser-based hair removal devices use bars of laser diodes to generate the light for the device. This typically requires the device to be capable of generating a large current to power the bars. Power supplies capable of producing such currents tend to be large and more expensive than power supplies producing less current. Additionally, larger currents produce more heat which can become a potential hazard if not handled effectively. If the efficiency of the device suffers at any point between the power supply and the targeted treatment area, even more power will be required to make the device function in a particular range. This also has the tendency to produce more heat, further complicating heat dissipation. Resolving heat dissipation can lead to additional or larger components which further detract from the ergonomics of the device and again prevent the useful application of laser removal methods for home use. Also, for safe use, it is important to understand the attributes of the targeted surface such as the type of skin or the presence of skin being targeted as well as to provide safe and secure use of the device. Accordingly, there is a need for a device that incorporates many of the aforementioned advantages and dispenses with the drawbacks.

SUMMARY OF THE INVENTION

The exemplary embodiment of a single-emitter diode based hair removal device, as disclosed herein, has several aspects which are designed to satisfy the aforementioned needs. One aspect relates to a light homogenizing apparatus that uses single-emitter laser diodes disposed adjacent to and capable of emitting into a highly transmissive light guide that refractively adjusts entering beams and homogenizes them so as to produce an output beam exiting the light guide that is substantially uniform in optical intensity across one or both dimensions generally transverse to propagation. The single-emitter diodes may be chosen so that each solid state diode emits at a selected wavelength or wavelength distribution. This allows the spectral power distribution of the final laser beam to be selected or varied for different applications. By comparison, in the current laser hair removal industry, beams tend to be monochromatically limited. Moreover, the use of a set of single-emitter diodes requires less power than a standard laser diode bar. Consequently, single-emitter diodes can be more efficient at generating light since less waste heat is generated, and when they are used in conjunction with laser hair removal the reduction in waste heat can allow for safer and smaller device configurations. Lower waste heat can result in a lower operating temperature which can allow more repeat usage of the device and a longer mean-time between failures as well. Thus, the use of one or more single-emitter diodes allows the system to remain smaller and safer, but also more rugged, reliable, and robust.

The laser light emitted from the diodes is coupled into a light guide made from a material with a high refractive index. The light guide is shaped to achieve total internal reflection of the laser light along at least one dimension and also minimizes the divergence angle of the light at the exit end of the light pipe. A low divergence angle of the light exiting the light pipe allows a greater amount of light to be directed at the target area rather than being wasted by being directed in an unproductive direction. It also reduces the need for additional expensive optics. The opposite walls of the light guide are tapered or expanded respectively, such that the entrance aperture of the light pipe is a rectangle and the exit aperture is a narrower square. This two-sided tapering reduces power loss by lowering the divergence angle of the exiting light, while shaping the light into an approximately uniform beam for use.

An optical diffuser is disposed after the light guide that includes an array or arrays of optical lenses, making the efficiency of light transmission through the diffuser very high. The diffuser spreads the power of the incoming light evenly over the area occupied by the exiting light, so that the fluence over the targeted area is more even and consistent but also causes the light to diverge widely to make the emitted beam eye-safe. While the aforementioned features are directed to claims in a co-pending application, cross-referenced above, the construction and function are illustrated and described herein for facilitating a complete and thorough understanding of the features of the system and claims of the present application.

The present invention relates to another feature of the hair removal device, such being the unique arrangement of sensors that detect the presence and color of a target surface in order to ensure safe application of the device. The skin presence sensor is situated in proximity to a window on the housing of the device and has a circuit that senses the capacitance of an object placed in proximity to or in contact with the housing. When the capacitance of skin is detected, the circuit is activated, allowing the laser hair removal device to function. The device or the light-generating components therein may be disabled if improper contact is detected in order to avoid misuse. Also, since darker skin tones absorb more light, laser hair removal can potentially be unsafe for different skin tones. For example, certain skin tones will absorb enough light to damage the surface skin layer, while less light will not damage the skin but will also not impact the hair or follicles. Therefore, the skin color detector is positioned in the device, preferably near the output of the device, and is configured to detect the color of the surface in proximity to it. If the skin color or tone is found to be in an unsafe category, the device can be rendered inoperable. Other features and advantages of the invention will be apparent from the following description of the preferred embodiments, and from the claims.

DETAILED DESCRIPTION OF THE INVENTION

In General

Figure 1:
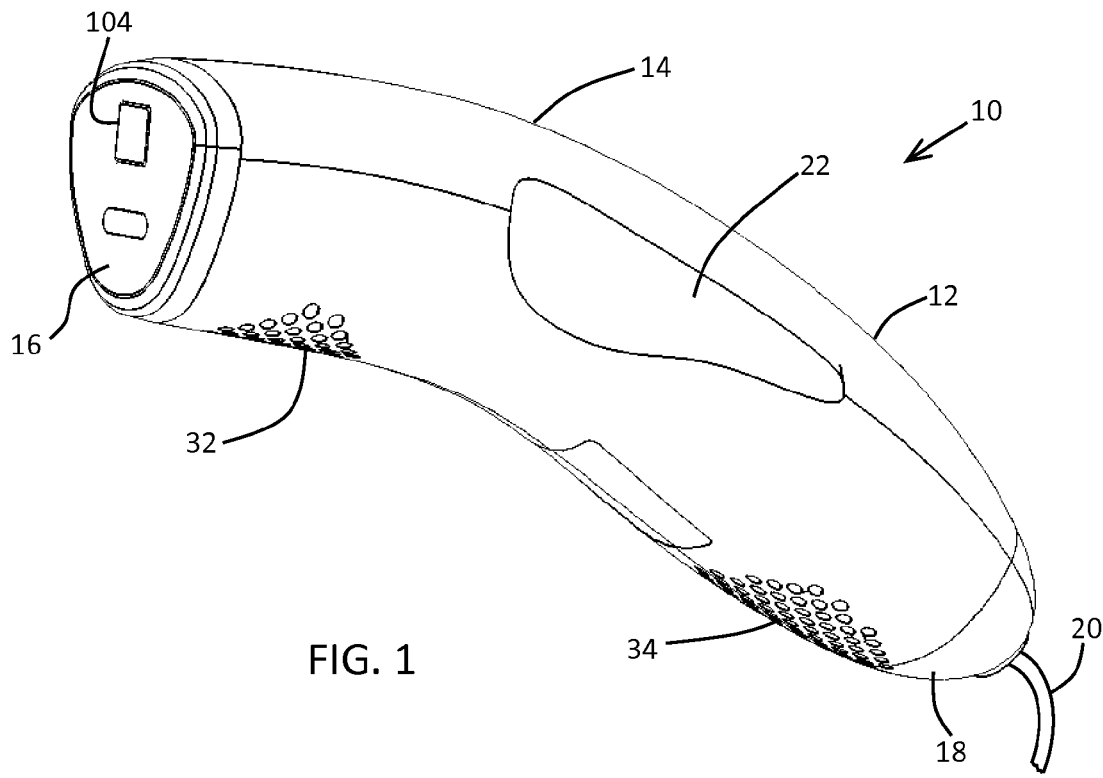
FIG. 1 is perspective view of a handheld hair removal device in accordance with the present invention.
Figure 2:
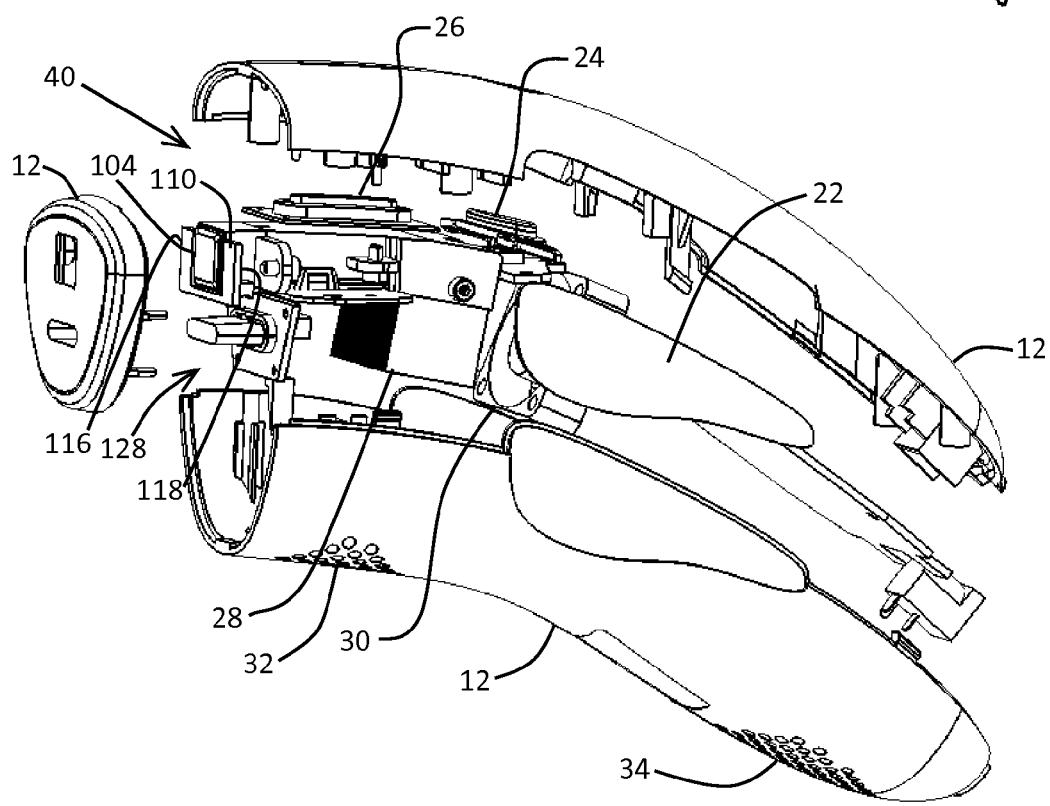
FIG. 2 is an exploded view of the hair removal device shown in FIG. 1.

Referring now to FIGS. 1 and 2, a hair removal device 10 is shown that is sufficiently compact and lightweight so that it may be held in one hand by a user. The device 10 has a housing 12 that includes an arcuate-shaped middle section 14 extending between opposite front and rear ends 16, 18, allowing for a comfortable and ergonomic grip by a user. The user positions the front end 16 of the device 10 towards a location on the body for application of radiative energy towards the epidermis such as for the removal of unwanted hair. Other embodiments of the device 10 may be used for other applications, such as for the removal of skin blemishes.

The rear end 18 receives electrical energy for powering the device via a cable 20 attached to a suitable external power supply (not shown). The aspect ratio of the housing 12 between the arcuate-shaped middle section 14 and the front and rear ends 14, 16 is large, thereby enabling the user of the device 10 to access harder to reach areas on the body. The middle section 14 includes a pair of opposite rubber grip portions 22 that provide a frictional area allowing the thumb and fingers of the user to easily grasp and direct the device 10 towards a target area of application. A button 24 is disposed at a top surface of the housing 12 so that the user may operate the device 10 with a forefinger while the device remains comfortably held. The user may select a power level and be provided with a visual indication thereof by way of an indication strip 26 disposed to emit light out the top surface of the housing 12 between the front end 16 and the button 24.

As shown in FIG. 2, the device 10 includes various components disposed within the housing 12 that allow for effective operation. Several of the heavier components, including for example a heatsink 28, are positioned closer to the front end 16, thereby situating much of the weight of the device 10 in proximity to the grip sides 22 and enhancing the ergonomics of the device. Additionally, a fan 30 that is operable to cool the heatsink 28 is positioned between the grip sides 22 and spins about an axis approximately in line with the longitudinal center of the arcuate middle section 14. The gyroscopic effect due to the positioning and spin direction of the fan 30 adds stability to the grip of the device 10 thereby also enhancing the effective application of the device. A first and second set of air-flow holes 32, 34 penetrating the bottom portion of the housing 12 allow air to flow in and out of the interior of the device 10 so that the fan 30 and heatsink 28 may work in conjunction to cool the device. The holes 32, 34 are placed out of the way of the grip by the user to ensure effective heat exchange by the device 10.

Light Homogenizing Apparatus

Figure 7:
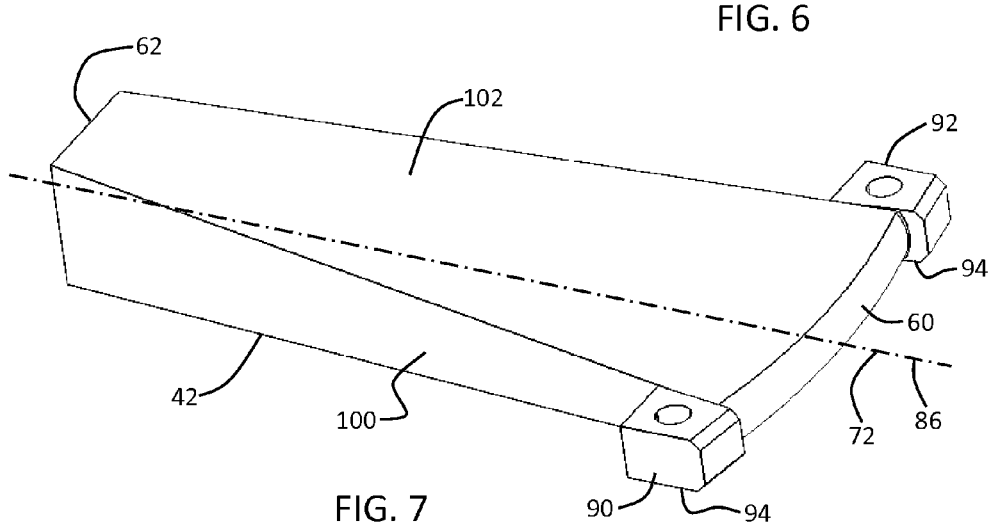
FIG. 7 is a perspective view of a light guide of the homogenizing apparatus shown previously in FIGS. 3 and 4 but now without additional components surrounding it.
Figure 8:
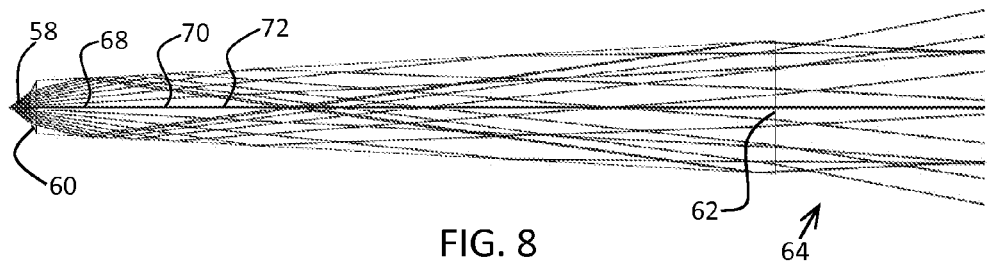
FIG. 8 is a side view ray tracing of light emitted by the laser diodes and propagated through the light guide according to an embodiment of the present invention.
Figure 9:
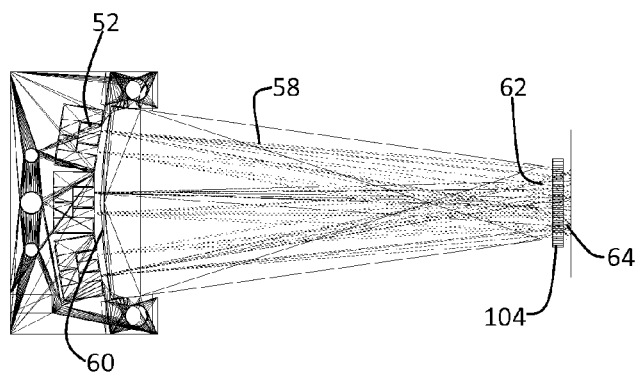
FIG. 9 is a top view ray tracing of light emitted by the laser diodes and propagated through the light guide according to an embodiment of the present invention.
Figure 10:
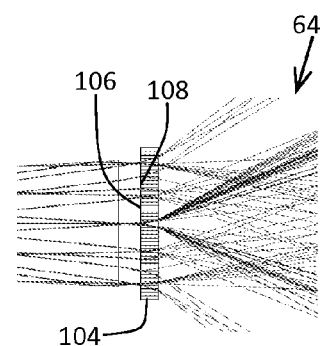
FIG. 10 is an expanded view of a side view ray tracing of light exiting the light guide and becoming diffused through a diffuser according to an embodiment of the present invention.
Figure 11:
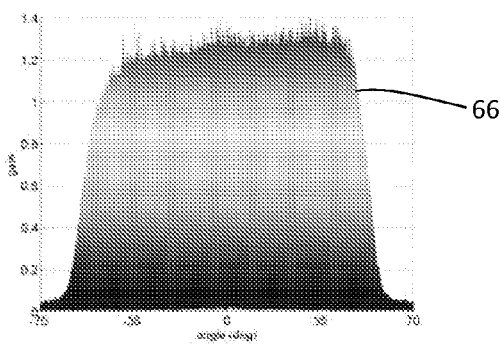
FIG. 11 is a graph of optical intensity across a range of divergence angles for light exiting the diffuser shown in FIG. 10.
Figure 12:
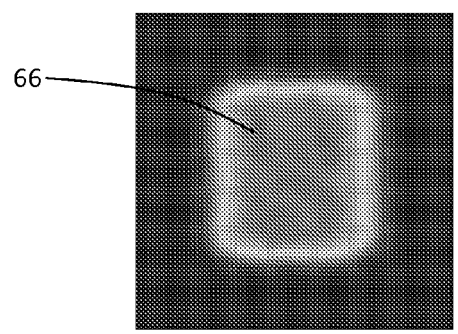
FIG. 12 is a graph of a substantially homogenized output beam in accordance with the present invention.

Referring now to FIGS. 2-7 a light homogenizing apparatus 40 is shown that is disposed within the housing 12 of the device 10. The apparatus 40 includes light guide 42 disposed adjacent to and optically coupled with a diode assembly 44. The diode assembly 44 includes a mounting subassembly 43 formed by a carrier plate 46 and one or more submounts 48 mounted upon the carrier plate 46. The carrier plate 46 is seated flush to a surface 96 of the heatsink 28, and a pair of fasteners 50 secures the light guide 42 and carrier plate 46 to the heatsink 28. The diode assembly 44 also includes one or more single-emitter laser diodes 52 that are mounted adjacent to each other on the one or more submounts 48 and are arranged so that an emitting end 54 of each emits light along a light path directed towards the light guide 42. The diodes 46 may be attached to or integrated with the carrier plate 46, however in the exemplary embodiment submounts 48 are used to enhance manufacturability. Beams 58 emitted from each emitting end 54 enter an input end 60 of the light guide 42 and propagate inside towards an output end 62. An output beam 64 exiting the output end 62 as seen in FIGS. 8-10 has a homogenized intensity profile 66, as depicted in FIGS. 11 and 12.

The laser diodes 52 may also be LEDs capable of producing an output beam of similar power, however as shown in FIGS. 3-6 and 9 each of the diodes 52 are laser diodes. In other hair removal devices, laser diode bars are typically used which tend to require large operating current, such as between 20 and 40 A. Higher operating currents tend to require larger and more expensive current supplies, more batteries, etc. However, by using single-emitter diode lasers 52 it is possible to produce 30 W of power using only 7 A. This enables the selection of a more compact and lower cost power supply to power the diodes 52. Additionally, the single emitter format combines with specialized optics described herein to allow for a compact and highly ergonomic laser hair removal device. If LEDs are to be used, they would have an alternative configuration within the scope of the present invention, and would include a plurality of LED chips (not shown) capable of producing more than 0.5 W each instead of laser diodes 52. A high density packaged LED array is capable of applying more than 50 W in a 10 mm by 10 mm area, and is therefore suitable for hair removal.

The laser diodes 52 may all be selected to emit radiation centered on a particular wavelength, such as 810 nm, or they may selected to emit at different wavelengths. For example, one pair may emit at 810 nm, a second pair at approximately 900 nm, and a third pair at approximately 1000 nm. Different wavelengths may be used for different applications and for different skin colors and may be selectably enabled by the device 10, such as by way of a skin color sensor assembly (described hereinafter) or a manual user selection. Thus, deeper penetration for darker skin tones can be achieved by using longer wavelengths. The diodes 52 are connected to each other in series with gold wire or other suitable contacting means and driven by approximately 1.85 V each. Thus, as shown the diodes 52 draw approximately 7 A from a 12 V power supply. Other configurations may be used and may be suitable, such as connecting two or more diodes in parallel, depending on the application.

Referring now to FIGS. 5 and 7-9, each laser diode 52 is capable of emitting a laser beam 58 with a chief ray 68 propagating through a plane 70 that is generally aligned with a length-wise middle cross-section 72 of the light guide 42. In the exemplary embodiment, the diodes 52 include six diodes 74A-F grouped in pairs, each diode emitting a respective beam 80A-F. Each pair has two single-emitter diode lasers 52 each mounted parallel to the other on a submount 78A-C so that the beams in each pair are emitted in the same direction. For example, diode lasers 74A, 74B on submount 78A emit parallel beams 80A, 80B having chief rays 82A, 82B at an angle α with respect to a central axis 86 and into plane 70. Diode lasers 74E, 74F are similarly mounted but with an opposite angle β with respect to central axis 86. Because of opposite angles α, β, the chief ray 82A of beam 80A is therefore normally configured to intersect chief ray 82F of beam 80F. Likewise, chief ray 82B of beam 80B is normally configured to intersect chief ray 82E of beam 80E. Diode lasers 74C, 74D are mounted so that the chief rays 82C, 82D of their respective beams 80C, 80D are directed into plane 70 parallel to the central axis 86. In other embodiments, diodes 52 may have beams directed into planes other than plane 70 and with different angles with respect to each other and with respect to the central axis 86.

Referring to FIGS. 3-9, the input end 60 of the light guide 42 is disposed adjacent to the submounts 48, which support the laser diodes 52, and has a pair of opposite mounting ears 90, 92 through which opposite holes are drilled. The mounting ears 90, 92 provide a bottom mating surface 94 allowing flush contact with recessed mounting tabs 46A, 46B of the carrier plate 46. The heatsink 28 is disposed below the carrier plate 46 and has a flat surface 96 configured to make flush contact with a bottom surface 98 of the carrier plate 46. Fasteners 50, such as hex socket head type fasteners, are first inserted through holes in the mounting ears 90, 92 of the light guide 42, next inserted through holes in the mounting tabs 46A, 46B of the carrier plate 46 and then fastened into threaded holes in the heatsink 28 so as to firmly secure the light guide 42 in a given orientation with respect to the carrier plate 46. In this way, in the exemplary embodiment the middle cross-section 72 of the light guide 42 is generally aligned with plane 70 into which the chief rays 68 of the beams 58 propagate. In other embodiments, different attaching mechanisms may be used to dispose the light guide 42, carrier plate 46, and heatsink 28 relative to each other, including but not limited to attaching them to or integrating them into the housing 12. Additionally, the middle cross-section 72 may be at an angle to plane 70.

Figure 3:
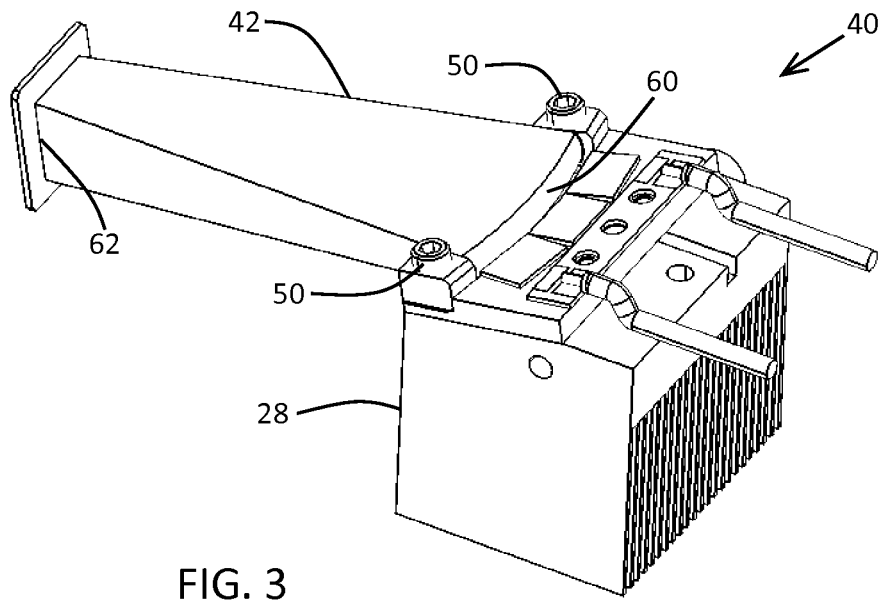
FIG. 3 is a perspective view of components of a light homogenizing apparatus in accordance with an embodiment of the present invention.

With respect to the exemplary embodiment, upon exiting the laser diodes 52, the beams 58 diverge considerably with respect to a first axis 84 that is vertical since the laser diodes 52 are oriented generally parallel with plane 70. Axis 84 is also referred to as the fast axis since the beam diverges the most across this axis. A corresponding second axis 88, that is horizontal and slow, i.e., where divergence is minimum, lies generally orthogonal to the fast axis 84 and the direction of the beam. When axes 84, 88 are extended in the direction of beam propagation they become planes having characteristic divergences. Also, depending on the geometry and composition of the diode 52 and the positioning of the diode 52 on the submount 48, a different divergence and relationship between the respective fast and slow axes can result. Separate collimation optics (not shown) may be disposed between the emitting ends 54 of the laser diodes 52 and the input end 60 of the light guide 42. However, as shown in FIG. 3, the light guide 42 is configured to provide the refractive adjustments normally provided by additional optics. As shown in FIGS. 3 and 7, the input end 60 has a sharply curved vertical contour and less sharply curved horizontal contour extending in a substantially orthogonal relationship to one another between the mounting ears 90, 92. The curved vertical contour refractively directs the diverging beams 58 to propagate through the interior of the light pipe, as shown in FIG. 8. The curved horizontal contour or bulge matches the respective positions of the laser diodes 52 relative to the input end 60 such that the distance between the emitting end 54 and the input end 60 is consistent or close to consistent across diodes.

Figure 4:
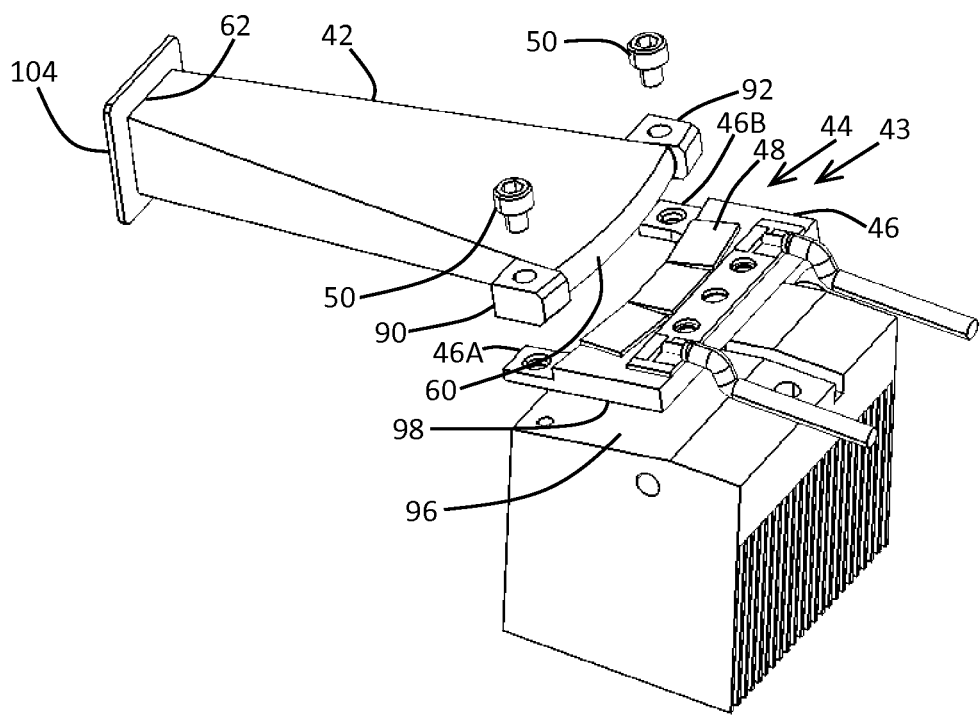
FIG. 4 is an exploded view of the homogenizing apparatus shown in FIG. 3.
Figure 5:
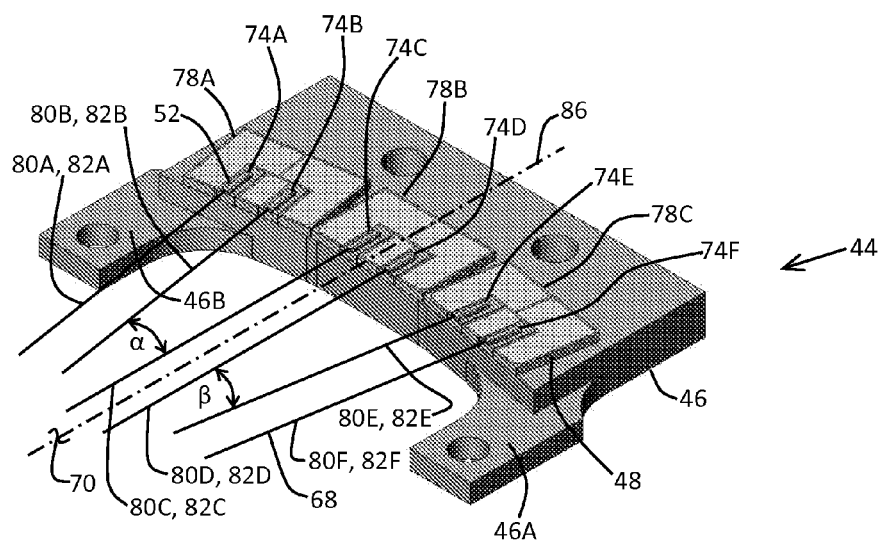
FIG. 5 is a perspective view of a mounting subassembly which is one of the components of the homogenizing apparatus according to an embodiment of the present invention.
Figure 6:
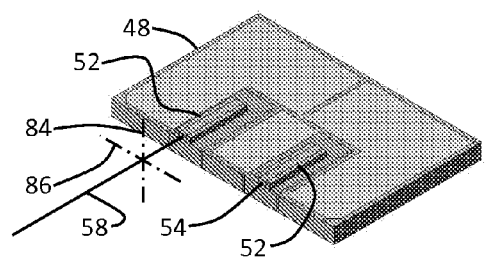
FIG. 6 is a perspective view of a pair of laser diodes mounted to a contact plate of the mounting subassembly shown in FIG. 5.

As best shown in FIGS. 3, 4 and 7, the light guide 42 includes a first pair of opposite walls 100 spaced apart from each other and a second pair of opposite walls 102 spaced apart from each other and extending transversely between the first pair of walls 100. Both pairs of opposite walls 100, 102 extend generally between the input and output ends 60, 62. The first pair or relatively vertical walls 100 increase in height linearly as the walls 100 extend from the input end 60 to the output end 62. Thus, as shown in FIG. 8, substantial portions of the beams 80C, 80D coupled into the input end 60 become reflected as the beams 58 propagate throughout the light guide 42. Similarly, other beams 80A, 80B and 80E, 80F become reflected throughout the interior of the light guide 42. The refractive index of the material comprising the light guide 42 is sufficiently large compared to media adjoining the second pair or relatively horizontal walls 102 such that total internal reflection is allowed for vertical reflections occurring throughout the interior of the light guide 42. Total internal reflection may be optimized by also considering the divergence correction achieved by the sharply curved vertical contour of the input end 60 hereinbefore described. The relatively horizontal walls 102 taper in width linearly as the walls 102 extend from the input end 60 to the output 62. As shown in FIG. 9, due to the orientation of the laser diodes 74A-F and the relatively low divergence across each slow axis thereof, the respective beams 80A-F do not interact substantially with the vertical walls 100 as they propagate through the interior of the light guide 42. However, in other embodiments light propagating through the light guide 42 interacts with vertical walls 100 so as to enhance horizontal homogenization of the output beam 64.

After expanding the height of the vertical walls 100 and tapering the height of the horizontal walls 102, the resulting output end 62 has a square to rectangular configuration of approximately 8 mm by 8 mm. As seen in FIGS. 1, 2, 9 and 10, a window 104 made from glass or other suitable material is disposed after the output end 62 and receives the output beam 64 emitting therefrom, and transmits the output beam 64 therethrough so that the output beam 64 may impinge the surface of a target substrate, such as the epidermis of a user. The light guide 42 described herein is highly transmissive, having an efficiency of greater than 90% and emitting light at the output end 62 with exit angles of less than +/−10°. Approximate operating parameters of the exemplary embodiment of the hair removal device 10 include a deposited pulse energy of between 9-20 J/cm$^2$, a treatment area of approximately 0.5 cm$^2$, a pulse length of between 0.2-0.5 s, a pulse repetition rate of 0.5 Hz, a homogenized intensity profile and exit angle of less than +/−10° produced by the light guide 42, and in a package having a weight of approximately 0.2 kg.

In order to make the output beam 64 eye-safe according to ANSI Z136.1 and IEC 60825 using the aforementioned operating parameters, the light of the output beam 64 should be made to diverge by more than one hundred degrees. Adding a typical diffuser to achieve eye-safe divergence, such as an opal or Lambertian type that scatters incoming light in all directions with a cosinusoidal distribution about an axis perpendicular to the scattering surface, would only allow transmission of less than 50% of input light into a usable forward cone. However, a suitable polymer based engineered surface, such as one made by RPC Photonics, can provide the requisite divergence for collimated input beams. Because the light guide 42 provides an output beam 64 that is relatively collimated, such an engineered surface may be included in the homogenizing apparatus 40 in order to achieve the required eye-safe divergence angle. As shown in FIGS. 9 and 10, diffusive engineered surface 106 is applied to the input end 108 of the window 104. The resulting output beam 64 has an eye-safe divergence angle and the transmission efficiency across the diffusing surface 106 is between 80% and 90%. The engineered surface 106 may also be applied elsewhere on the homogenizing apparatus, such as to the input end 60 of the light guide 42. The intensity profile 66 of the homogenized output beam 64 produced by the homogenizing apparatus 40 with the engineered surface 106 applied to the window 104 is shown in FIGS. 11 and 12. FIG. 11 shows that the intensity profile 66 has losses minimized outside the imposed divergence angle requirement and FIG. 12 shows the substantial consistency across two dimensions of the intensity profile 66 of the output beam 64 exiting the window 104.

Sensor System and Assembly

Figure 13:
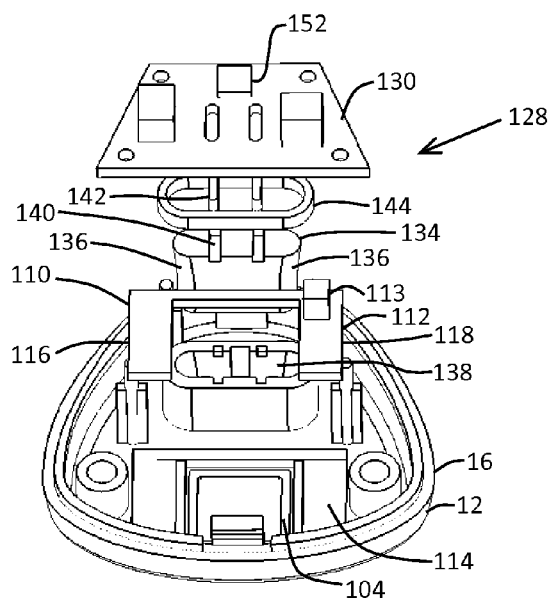
FIG. 13 is an exploded view of the front portion of the hair removal device that includes a skin color sensor and a skin contact sensor according to an embodiment of the present invention.
Figure 14:
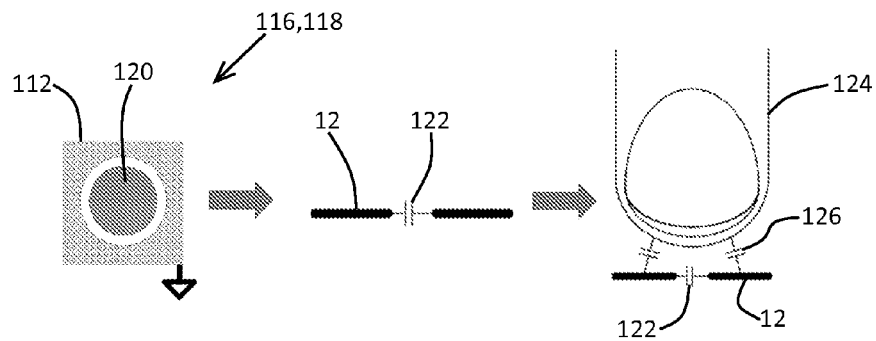
FIG. 14 is a schematic diagram showing the application of the skin contact sensor works in accordance with the present invention.

Referring to FIGS. 2 and 13-15, the hair removal device 10 is shown to include one or more sensor assemblies disposed near the front end 16. In order to ensure that the device 10 is contacting the surface of the person's body, a sensor assembly 110 for detecting touch capacitance is positioned inside the housing 12 and near the output window 104. As shown in FIG. 13 in exploded view, the sensor assembly 110 includes a printed circuit board member 112 that provides a base for the sensor assembly 110 and fits into a relief area 114 that surrounds the window 104 on three sides. Two capacitance sensors 116, 118 are disposed on the underside of the member 112 and contact the inside surface of the front end 16 of the housing 12. The sensors 116, 118 are wired to a logic circuit attached to the printed circuit board member 112. As schematically illustrated in FIG. 14, the sensors 116, 118 detect a change in capacitance through the housing 12 by way of the presence of human touch. The sensor 116 includes a copper piece 120 attached to the pcb member 112 and that is grounded and in series with a microcontroller 113 shown in FIG. 13. The housing 12 provides a base capacitance 122 and contact with a person, such as with a finger 124, provides additional capacitance 126 that is sensed by the microcontroller 113. Second sensor 118 is positioned on the opposing side of the pcb member 112. Additional sensors may be included to surround the device, though two sensors are sufficient to ensure sufficient proximity between the housing 12 and the skin surface. Thus, when sufficient proximity is not sensed, the microcontroller 113 can enable the device 10 to become inoperable.

Figure 15:
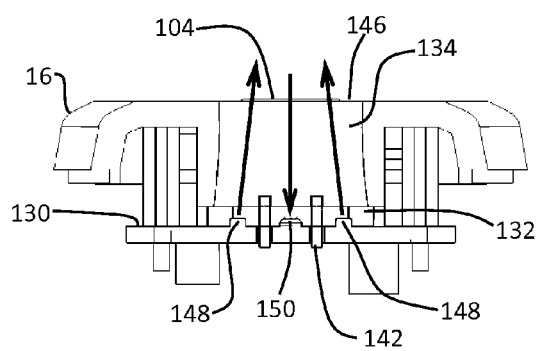
FIG. 15 is an expanded cross-sectional view of the front portion of the hair removal device showing the light path of the skin color sensor in accordance with an embodiment of the present invention.

Referring to FIGS. 2, 13 and 15, the hair removal device 10 is also shown to include a skin color sensing assembly 128. The assembly 128 basically includes a printed circuit board member 130, a holder member 132, and a light pipe 134. The light pipe 134 has opposite curved ends 136 with a rectangular profile therebetween, and is shaped so as to fit into a similarly shaped cavity 138 molded into the housing 12. The light pipe 134 also has a pair of relief notches 140 cut into a top or inner surface thereof. The holder 132 includes a pair of standoff supports 142 interposed between an outer ring halves 144 having similar geometry to the light pipe 134. The bottom ends of the supports 142 fit into the relief notches 140 of the light pipe 134 and the top ends of the supports 142 fit into holes cut into the pcb member 130. With compression, adhesive, clasps, or other suitable means, the holder 132 fits between and secures the light pipe 134 and the pcb member 130 of the skin color assembly 128. The light pipe 134 then fits into the cavity 138 and has bottom surface that becomes exposed to the exterior of the housing 12 through a color sensor aperture 146. Thus, the skin color sensing assembly 128 becomes disposed in the housing 12 in proximity to the window 104 that transmits the output beam 64 of the device. In other embodiments, the skin color sensing assembly 128, or skin color sensor aperture 146, or both, is disposed away from the window 104.

The printed circuit board member 130 of the color sensing assembly 128 has a pair of light emitting diodes 148 situated on opposite sides of the standoff supports 142 and directed to emit toward the light pipe 134. A sensor array 150 is situated on the pcb member 130 interposed between the standoff supports 142. As shown by the direction arrows in the cross-sectional view of the assembly 128 in FIG. 15, light emitted by LEDs 148 propagates through side emission propagation regions of the light pipe 134 and some portion of that light becomes reflected off a surface, such as skin positioned in proximity to the aperture 146, back through a middle receiving propagation region of the light pipe 134 and is received at the sensor array 150. The relief notches 140 and respective standoff supports 142 help define these regions by blocking light emitted by the LEDs 148 from propagating directly to the sensor array 150. A microcontroller 152 shown in FIG. 13 receives a signal from the sensor array 150 and computes a value that can inform the user of the device 10 of the viability of application to the surface in question. The LEDs 148 can be white LEDs that emit light into a relatively broad spectrum. The sensor array 150 then detects particular wavelengths that have been reflected back and the microcontroller 152 can form a composite value based on the relative quantities of reflected light. For composite values outside of a particular cutoff value the device 10 can be rendered inoperable. The skin color sensing assembly 128 and associated color sensor aperture 146 may be positioned elsewhere on the device 10 as needed.

The combination of sensor assemblies 110, 128 may be applied to other devices as well. For example, a handheld device may include a security feature wherein functionality requires both the detection of skin contact and the detection of a particular skin color or tone. Such a parent device may be one where safety or injury-risk avoidance is a concern, such as a laser hair removal device 10 as described in detail above. Another parent device may be one where security is more of a concern such as an electrical device like a handheld portable communications device. Here the combinations of sensor assemblies 110, 128 may serve a lockout function or a personal identity recognition function. Thus, the parent device may only be operated by a user physically operating the device and that matches a particular skin color profile.

It is thought that the present invention and many of the attendant advantages thereof will be understood from the foregoing description and it will be apparent that various changes may be made in the parts thereof without departing from the spirit and scope of the invention or sacrificing all of its material advantages, the form hereinbefore described being merely an exemplary embodiment thereof.

What is claimed is:

1. A sensor system for a hair removal device, comprising:
    a housing having a color sensor aperture;
    a color sensor assembly including a color sensor disposed in said housing and spaced from said color sensor aperture, a light pipe interposed between said aperture and color sensor and having emitting and receiving light propagation regions defined therein, said color sensor being optically coupled to said receiving light propagation region, and at least one light emitting diode positioned near said sensor and optically coupled to a respective emitting propagation region such that said color sensor is capable of detecting the color of a surface placed in communication with said color sensor aperture by receiving light reflected from the surface that is emitted by said light emitting diode;
    a surface member having said color sensor mounted thereon; and
    a holder interposed between an inner end of said light pipe and said surface member;
    wherein said light pipe has one or more notches defined in said inner end and said holder has one or more standoffs protruding from an outer end of said holder and inserted into said one or more notches of said light pipe so as to define said light propagation regions of said light pipe.

2. The sensor system of claim 1 further comprising:
    said housing also having a device aperture; and
    a capacitive sensor assembly including one or more capacitive sensors disposed in said housing near said device aperture thereof, for detecting the presence of an object having capacitance and in contact with an outside surface of said housing.

3. The sensor system of claim 2 wherein said color sensor aperture is near said device aperture.

4. The sensor system of claim 1 wherein said light pipe has an outer end disposed flush with said outside surface of said housing.

5. The sensor system of claim 1, wherein said one or more notches includes two notches such that said standoffs defines two emitting propagation regions each on opposite outer sides of said notches and defines one receiving propagation region interposed between opposite inner sides of said notches, and wherein said at least one light emitting diode includes two light emitting diodes each situated on said surface member.

6. The sensor system of claim 1, wherein said at least one light emitting diode emits broadband light.

7. The sensor system of claim 1, wherein said color sensor is an array of filtered diodes each diode capable of detecting one of red, green, blue, or broadband light.

8. A sensor system, comprising:
    a housing;
    a light pipe including an input end, an output end, and one or more standoff notches protruding into said input end, said light pipe being disposed in said housing with said output end positioned relative to a color sensor aperture of said housing;
    a sensor array disposed on a surface member, said surface member also having one or more holes;
    a holder including one or more standoffs each having a top and bottom end, said top end being insertable into a respective one of said one or more surface member holes and securable therewith, and said bottom end insertable into a respective one of said one or more standoff notches and securable therewith, said one or more standoffs thereby defining a receiving propagation region and one or more emission propagation regions of said light pipe; and
    one or more light emitting diodes disposed in said housing each directed to emit light through a respective one of said emission propagation regions and out said color sensor aperture so as to reflect said light off a target surface and back in said aperture and through said receiving propagation region for receipt by said sensor array.

9. The sensor system of claim 8, wherein said housing has an arcuate shape and slender contour suitable for gripping at a middle section thereof.

10. The sensor system of claim 9, further comprising a light homogenizing apparatus disposed in said housing and communicating with a device aperture defined through a front portion of said housing, said device aperture lying in proximity to said color sensor aperture.

11. The sensor system of claim 8, further comprising a capacitive sensor assembly disposed in said housing and including a plurality of copper sensor elements contacting an inner surface of said housing in proximity to a device aperture and communicating with a microcontroller, said sensor elements being capable of detecting a change in capacitance through said housing due to an object in contact with an outer surface thereof overlying said copper sensor elements.

* * * * *